United States Patent
Nakayama et al.

(10) Patent No.: US 12,220,231 B2
(45) Date of Patent: Feb. 11, 2025

(54) ESTIMATION DEVICE AND ESTIMATION METHOD

(71) Applicant: Panasonic Intellectual Property Management Co., Ltd., Osaka (JP)

(72) Inventors: Takeshi Nakayama, Hyogo (JP); Shoichi Iizuka, Osaka (JP); Naoki Honma, Iwate (JP); Nobuyuki Shiraki, Iwate (JP); Teppei Hayashi, Iwate (JP); Kazuki Numazaki, Iwate (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 429 days.

(21) Appl. No.: 17/612,362

(22) PCT Filed: Dec. 28, 2020

(86) PCT No.: PCT/JP2020/049131
§ 371 (c)(1),
(2) Date: Nov. 18, 2021

(87) PCT Pub. No.: WO2021/140988
PCT Pub. Date: Jul. 15, 2021

(65) Prior Publication Data
US 2022/0233103 A1    Jul. 28, 2022

(30) Foreign Application Priority Data
Jan. 7, 2020   (JP) ................................ 2020-000876

(51) Int. Cl.
*G01S 13/88*    (2006.01)
*A61B 5/107*    (2006.01)
(Continued)

(52) U.S. Cl.
CPC ............ *A61B 5/1171* (2016.02); *A61B 5/107* (2013.01); *G01S 3/143* (2013.01); *G01S 7/02* (2013.01);
(Continued)

(58) Field of Classification Search
CPC ..... A61B 5/1171; A61B 5/107; A61B 5/1114; A61B 5/1126; A61B 5/6889;
(Continued)

(56) References Cited

U.S. PATENT DOCUMENTS

2010/0152600 A1   6/2010   Droitcour et al.
2016/0161450 A1*   6/2016   Moreau ................ G01N 29/069
                                              73/598

(Continued)

FOREIGN PATENT DOCUMENTS

CN        107788992 A *   3/2018   .......... A61B 5/0077
JP        2007-325621 A    12/2007

(Continued)

OTHER PUBLICATIONS

International Search Report and Written Opinion issued on Feb. 2, 2021 in International Patent Application No. PCT/JP2020/049131; with partial English translation.

(Continued)

*Primary Examiner* — Timothy A Brainard
*Assistant Examiner* — Ismaaeel A. Siddiquee
(74) *Attorney, Agent, or Firm* — Rimon P.C.

(57) ABSTRACT

An estimation device includes: M transmission antenna elements each transmitting a first transmission signal; N transmitter-receivers each including a reception antenna element and receiving, over a predetermined period, a first reception signal including a reflection signal that is the first transmission signal reflected by a first living body, using the reception antenna element; a memory storing training sig- (Continued)

nals that are second reception signals obtained by causing the N transmitter-receivers to preliminarily receive second reception signals including reflection signals that are second transmission signals transmitted from the M transmission antenna elements to a second living body and reflected therefrom; a first vector calculator calculating a first vector for each training signal and each first reception signal by respective predetermined methods; and a circuit identifying the first living body or estimating an orientation of the first living body by a predetermined method, using correlation coefficients calculated from the first vectors.

9 Claims, 11 Drawing Sheets

(51) Int. Cl.
| | |
|---|---|
| *A61B 5/1171* | (2016.01) |
| *G01S 3/14* | (2006.01) |
| *G01S 7/02* | (2006.01) |
| *A61B 5/00* | (2006.01) |
| *A61B 5/0507* | (2021.01) |
| *A61B 5/11* | (2006.01) |
| *G01S 7/41* | (2006.01) |
| *G01S 13/00* | (2006.01) |
| *G01S 13/87* | (2006.01) |

(52) U.S. Cl.
CPC ............ *G01S 13/88* (2013.01); *A61B 5/0507* (2013.01); *A61B 5/1114* (2013.01); *A61B 5/1126* (2013.01); *A61B 5/6889* (2013.01); *A61B 5/7267* (2013.01); *A61B 2503/12* (2013.01); *A61B 2505/07* (2013.01); *A61B 2562/0228* (2013.01); *G01S 7/415* (2013.01); *G01S 13/003* (2013.01); *G01S 13/874* (2013.01)

(58) Field of Classification Search
CPC .............. A61B 5/7267; A61B 2503/12; A61B 2505/07; A61B 2562/0228; A61B 5/0507; G01S 3/143; G01S 7/02; G01S 13/88; G01S 7/415; G01S 13/003; G01S 13/874
See application file for complete search history.

(56) References Cited

U.S. PATENT DOCUMENTS

| | | | |
|---|---|---|---|
| 2017/0205502 | A1 | 7/2017 | Honma et al. |
| 2018/0055437 | A1* | 3/2018 | Nakayama ............... A61B 5/74 |
| 2018/0192919 | A1* | 7/2018 | Nakayama ............ A61B 5/1116 |
| 2019/0158494 | A1 | 5/2019 | Nakayama et al. |
| 2019/0212431 | A1 | 7/2019 | Iizuka et al. |
| 2019/0339379 | A1 | 11/2019 | Iizuka et al. |
| 2020/0285894 | A1* | 9/2020 | El-Khamy ............ G06F 18/214 |

FOREIGN PATENT DOCUMENTS

| | | | | |
|---|---|---|---|---|
| JP | 2009-055997 A | | 3/2009 | |
| JP | 2015-042293 A | | 3/2015 | |
| JP | 2017116519 A | * | 6/2017 | ........... G01S 13/003 |
| JP | 2019-093104 A | | 6/2019 | |
| JP | 2019-197039 A | | 11/2019 | |
| JP | 2019-211458 A | | 12/2019 | |

OTHER PUBLICATIONS

Teppei Hayashi, et al., "Non-Constraint Estimation Method of Human Orientation Using Multi-Static MIMO Radar", Proceedings of the 2020 IEICE General Conference, pp. 150, Mar. 2020 with English translation.

Extended European Search Report dated Jun. 7, 2023 issued in the corresponding European Patent Application No. 20912494.0.

* cited by examiner

FIG. 10

| (x, y) | y = 1 | y = 2 | y = 3 |
|---|---|---|---|
| x = 1 | 88.9 | 94.4 | 83.3 |
| x = 2 | 88.9 | 88.9 | 77.8 |
| x = 3 | 80.6 | 88.9 | 75.0 |

(Average percentage of data correctness of 3 persons)

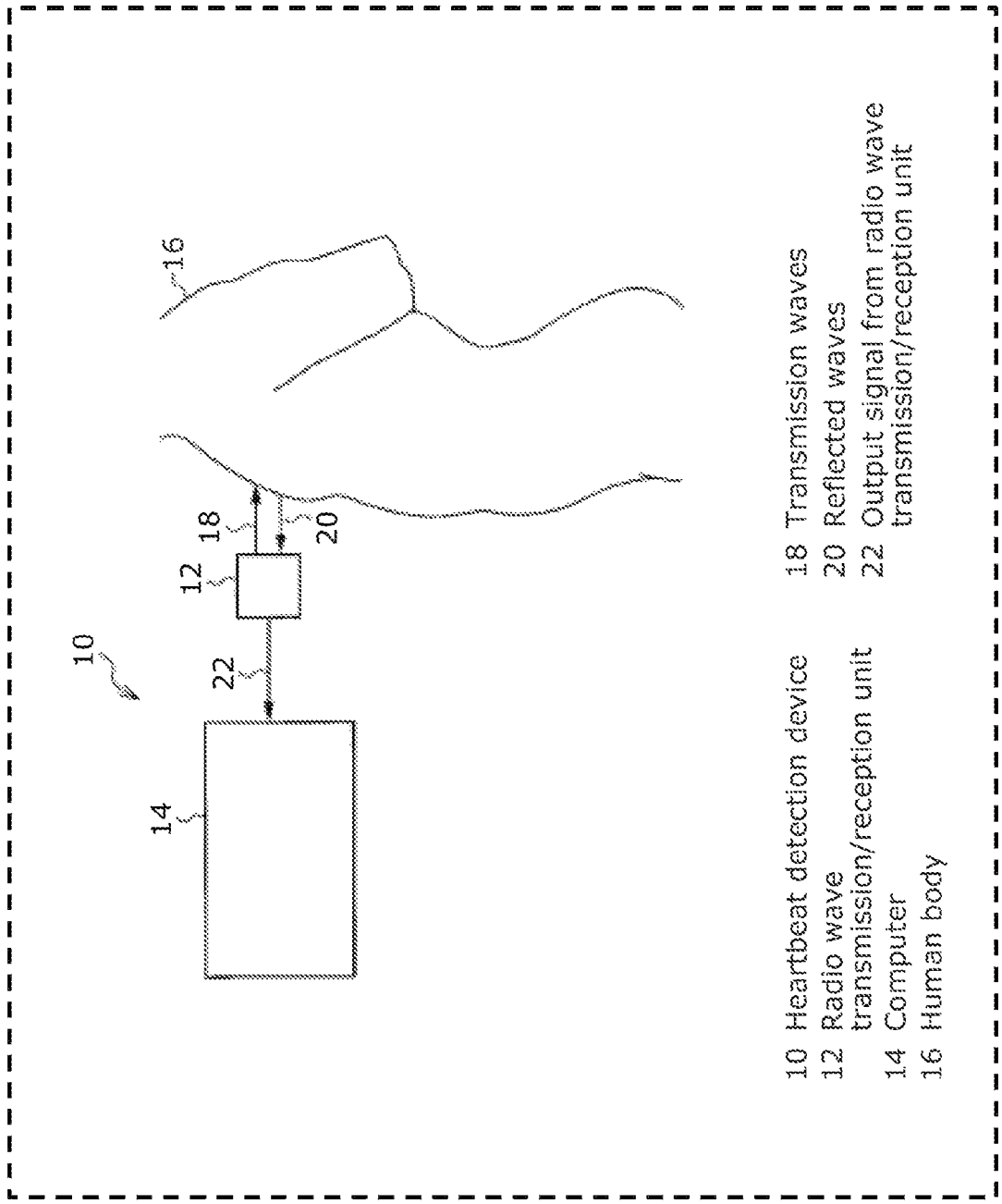

ESTIMATION DEVICE AND ESTIMATION METHOD

CROSS-REFERENCE OF RELATED APPLICATIONS

This application is the U.S. National Phase under 35 U.S.C. § 371 of International Patent Application No. PCT/JP2020/049131, filed on Dec. 28, 2020, which in turn claims the benefit of Japanese Application No. 2020-000876, filed on Jan. 7, 2020, the entire disclosures of which Applications are incorporated by reference herein.

TECHNICAL FIELD

The present disclosure relates to an estimation device and an estimation method that radiate a wireless signal to a living body and receive a reflection signal therefrom to identify the living body or estimate the orientation of the living body.

BACKGROUND ART

Technologies have been known for radiating a wireless signal to a living body and receiving a reflection signal therefrom to identify/estimate the living body or estimate the orientation of the living body (see, for example, Patent Literature (PTL) 1 and PTL 2). PTL 1 discloses a device that estimates the driver of an automobile by radiating electromagnetic waves to the driver and extracting the heartbeats and heat sound signals, using reflected waves from the driver. PTL 2 discloses a method of measuring the heart rate of the driver of an automobile, who is a test subject, using a plurality of transmitter-receivers.

Another example is PTL 3 that discloses a device that measures patterns of 360-degree radiation to the test subject, using a plurality of antennas. Further another example is PTL 4 that discloses an identification device that identifies an individual using a plurality of antennas disposed near the test subject.

Further another example is PTL 5 that discloses an estimation device that estimates the orientation of a living body, using a plurality of antennas disposed near the test subject.

CITATION LIST

Patent Literature

[PTL 1] Japanese Unexamined Patent Application Publication No. 2015-042293
[PTL 2] Japanese Unexamined Patent Application Publication No. 2009-055997
[PTL 3] Japanese Unexamined Patent Application Publication No. 2007-325621
[PTL 4] Japanese Unexamined Patent Application Publication No. 2019-93104
[PTL 5] Japanese Unexamined Patent Application Publication No. 2019-211458

SUMMARY OF INVENTION

Technical Problem

In many cases, identification of a living body or estimation of the orientation of the living body utilizing electromagnetic waves are performed under a condition that a person to be measured and antennas are located relatively close to each other as shown in PTL 1, PTL 2, PTL 4, and PTL 5.

That the test subject and the antennas need to be located close to each other is unlikely to be a problem for the identification of an individual in a narrow area such as a driver's seat and an individual room. Such limitation, however, poses a problem that individual identification is hard to be performed in a situation in daily life, etc.

The present disclosure has been conceived in view of the above circumstances, and its aim is to provide an estimation device and an estimation method capable of identifying a living body or estimating the orientation of the living body by use of electromagnetic waves even under a condition that a test subject and antennas are spaced apart from each other in, for example, an indoor place.

Solution to Problem

The estimation device according to an aspect of the present disclosure is: an estimation device that identifies a living body or estimates an orientation of the living body, the estimation device including: M transmission antenna elements each transmitting a first transmission signal to a predetermined range that includes a first living body, where M is an integer greater than or equal to 1; N receivers disposed to surround the predetermined range, where N is an integer greater than or equal to 3, the N receivers each including a reception antenna element that receives, over a predetermined period, a first reception signal that is the first transmission signal reflected by the first living body; a memory that stores training signals which are (M×N) second reception signals obtained by causing each of the N receivers to preliminarily receive a second reception signal that is a second transmission signal transmitted from each of the M transmission antenna elements and reflected by a second living body; a first vector calculator that calculates a first vector for each of the training signals and each of (M×N) first reception signals by respective predetermined methods, the (M×N) first reception signals being obtained by the N receivers each receiving the first reception signal; and an estimator that calculates a plurality of correlation coefficients from the first vectors and identifies the first living body or estimates an orientation of the first living body by a predetermined method, using the plurality of correlation coefficients calculated.

These general and specific aspects may be implemented using a system, a method, an integrated circuit, a computer program, or a computer-readable recording medium such as a CD-ROM, or any combination of systems, methods, integrated circuits, computer programs, or computer-readable recording media.

Advantageous Effects of Invention

The estimation device according to the present disclosure is capable of identifying a living body or estimating the orientation of the living body by use of electromagnetic waves even under a condition that a test subject and antennas are spaced apart from each other in, for example, an indoor place.

BRIEF DESCRIPTION OF DRAWINGS

FIG. 10 is a diagram showing an exemplary data correctness for three persons.

FIG. 11 is a diagram showing the configuration of PTL 1.

Figure 1:
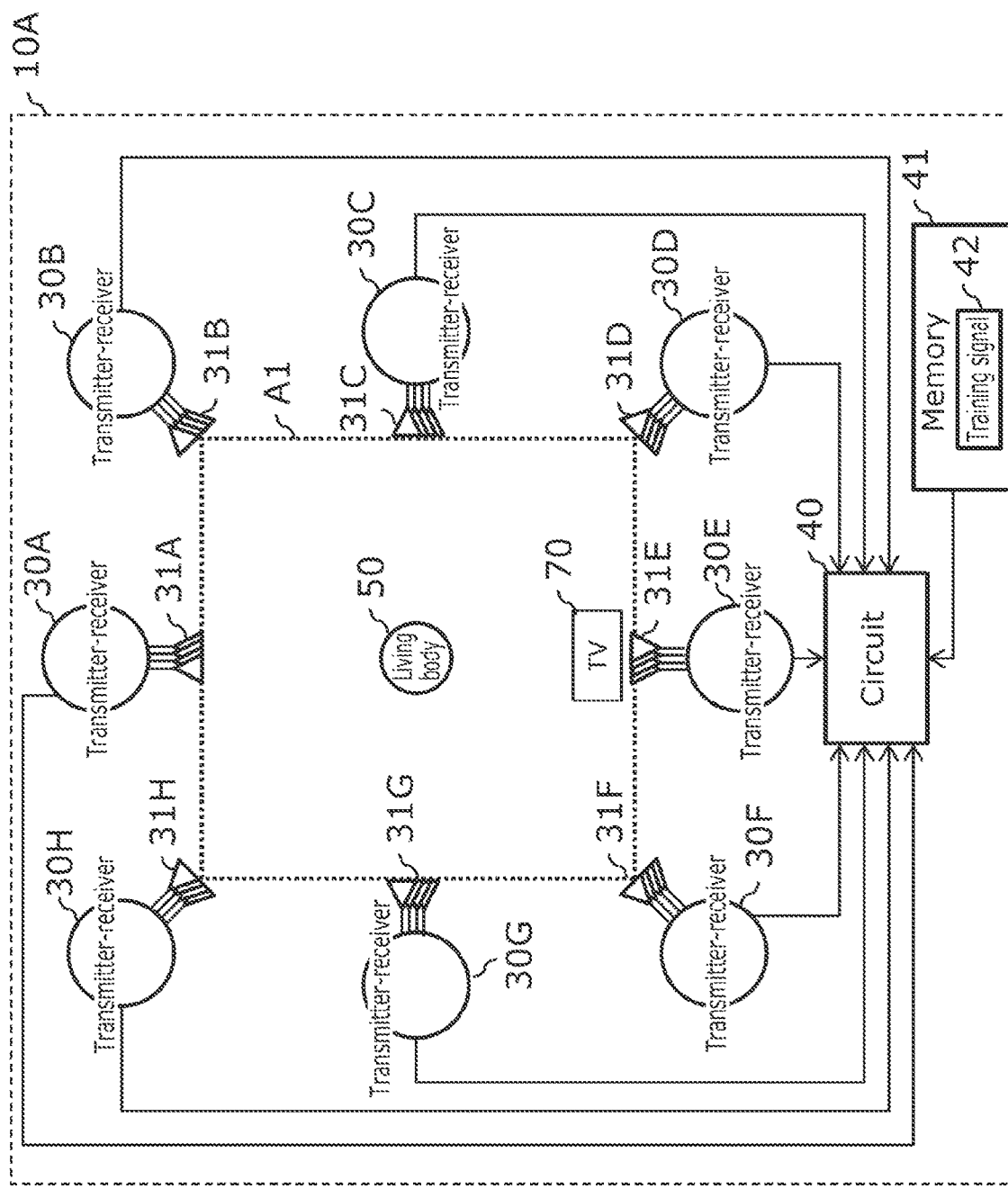
FIG. 1 is a configuration diagram showing an exemplary configuration of an estimation device according to the embodiment.

DESCRIPTION OF EMBODIMENT (Underlying Knowledge Forming Basis of the Present Disclosure)

In PTL 1 and PTL 2, electromagnetic waves are radiated to a person seated in the driver's seat of an automobile to measure reflected waves from the person. Subsequently, computation is performed on the measurement result to measure the heartbeats or heat sounds, and then a temporal correlation of the measured heartbeats or heart sounds is obtained to identify the living body.

However, PTL 1 has a problem, as described above, that its method is operable only in a limited environment, such as a narrow space like the driver's seat, where the positions of the test subject and the antennas are identifiable. For this reason, in a situation in daily life such as an indoor place, identification of a living body or estimation of the orientation of the living body is required to be performed under a condition that the antennas and the test subject are spaced apart from each other, with a flexibility given to the positional relationship between the antennas and the test subject.

The inventors have spent much time to study the foregoing problem to find the points described below that are required for the identification of a living body or estimation of the orientation of the living body by use of electromagnetic waves, even under a condition that the test subject and the antennas are spaced apart from each other such as in an indoor place. That is to say, antenna elements are disposed around the room in which a target individual to be identified is active to transmit transmission waves from various directions and receive reflected waves and scattered waves in various directions, thereby obtaining reception signals capturing a larger number of features of the living body.

The reception signals vary, to no small extent, depending on the distance between the living body and an antenna or the orientation or posture of the living body. As such, to identify the living body or estimate the orientation of the living body, training data needs to be obtained while estimating the position or posture of the living body from the reception signals and the position or posture of the living body is stored as an identified position. At this time, the intensity of reception signals is relatively high when the distance between the antenna and the test subject is sufficiently short as in the background arts such as in PTL 1 and PTL 2, and thus the identification of an individual or the estimation of the orientation of the living body is feasible. However, when the identification of the living body is performed using electromagnetic waves in an indoor place, etc. where the test subject and the antennas are spaced apart from each other, the intensity of reception signals becomes low due to distance attenuation. This makes it hard to distinguish between the reception signals and noise floor, thus reducing the accuracy of identifying the individual or estimating the orientation of the living body.

In view of the above, the inventors have found that it is possible to know whether the living body to be measured is present in the training data or to accurately identify the orientation of such living body in the following manner, even in an area such as a housing space: decompose a correlation matrix into eigenvalues; reorder the result in order of eigenvalues; extract channels that include many vital components and remove DC components therefrom; and calculate a correlation with the training data after the test subject makes the same posture in the identified position.

The estimation device according to an aspect of the present disclosure is an estimation device that identifies a living body or estimates an orientation of the living body, the estimation device including: M transmission antenna elements each transmitting a first transmission signal to a predetermined range that includes a first living body, where M is an integer greater than or equal to 1; N receivers disposed to surround the predetermined range, where N is an integer greater than or equal to 3, the N receivers each including a reception antenna element that receives, over a predetermined period, a first reception signal that is the first transmission signal reflected by the first living body; a memory that stores training signals which are (M×N) second reception signals obtained by causing each of the N receivers to preliminarily receive a second reception signal that is a second transmission signal transmitted from each of the M transmission antenna elements and reflected by a second living body; a first vector calculator that calculates a first vector for each of the training signals and each of (M×N) first reception signals by respective predetermined methods, the (M×N) first reception signals being obtained by the N receivers each receiving the first reception signal; and an estimator that calculates a plurality of correlation coefficients from the first vectors and identifies the first living body or estimates an orientation of the first living body by a predetermined method, using the plurality of correlation coefficients calculated. Note that the first vectors correspond to, for example, a training first vector and a test first vector. The estimator corresponds to, for example, the circuit.

With this, it is possible to calculate a plurality of correlation coefficients from the training signals and the first reception signals that are measurement signals obtained from the reception antenna elements disposed around the first living body. Subsequently, depending on whether the maximum value of the plurality of correlation coefficients exceeds a threshold, it is possible to estimate whether the first living body and the second living body that is included in the training data are in the same orientation. Alternatively, it is possible to authenticate the living body by identifying whether the first living body and the second living body that is included in the training data are identical.

For example, the first vector calculator may include: a second matrix calculator that calculates a second matrix from the first reception signals; a decomposer that decomposes the second matrix by a predetermined method and reorders elements of the second matrix by a predetermined method, and calculate the first vectors, using the elements of the second matrix that have been reordered and the training signals or the first reception signals.

For example, the decomposer may decompose the second matrix into eigenvalues and reorder, in descending order, the eigenvalues that are diagonal elements.

For example, the decomposer may decompose the second matrix into singular values and reorder, in descending order, the singular values that are diagonal elements.

For example, the first vector calculator may remove, by a predetermined method, a DC component from the first vectors calculated.

For example, the estimator may calculate, by a predetermined method, a total number of correlation functions to be used among a plurality of correlation matrices and calculate a total sum of correlation matrices for an amount equivalent to the total number of correlation functions to be used.

For example, to estimate an orientation of the first living body, the estimator may store training signals for respective orientations of a living body, and estimate, as the orientation of the first living body, an orientation of one of the training signals that corresponds to a maximum of the total sum of the plurality of correlation matrices.

With this, it is possible to accurately identify whether the training data includes a living body that is in the same orientation as that of the living body to be measured, even in an area such as a housing space.

For example, to identify the first living body, the estimator may store training signals in a same orientation for each living body, and estimate, as a living body identical to the first living body, one of the training signals that corresponds to a maximum of the total sum of the plurality of correlation matrices.

With this, it is possible to accurately identify whether the training data includes the living body to be measured, even in an area such as a housing space.

Also, the living body position estimation method according to an aspect of the present disclosure is an estimation method performed by an estimation device that identifies a living body or estimates an orientation of the living body, wherein the estimation device includes: M transmission antenna elements each transmitting a first transmission signal to a predetermined range that includes a first living body, where M is an integer greater than or equal to 1; N receivers disposed to surround the predetermined range, where N is an integer greater than or equal to 3, the N receivers each including a reception antenna element that receives, over a predetermined period, a first reception signal that is the first transmission signal reflected by the first living body; and a memory that stores training signals which are (M×N) second reception signals obtained by causing each of the N receivers to preliminarily receive a second reception signal that is a second transmission signal transmitted from each of the M transmission antenna elements and reflected by a second living body; wherein the estimation method includes: calculating a first vector for each of the training signals and (M×N) first reception signals by respective predetermined methods, the (M×N) first reception signals being obtained by the N receivers each receiving the first reception signal; and calculating a plurality of correlation coefficients from the first vectors and identifying the first living body or estimating an orientation of the first living body by a predetermined method, using the plurality of correlation coefficients calculated.

Note that these general and specific aspects may be implemented using a system, a method, an integrated circuit, a computer program, or a computer-readable recording medium such as a CD-ROM, or any combination of systems, methods, integrated circuits, computer programs, or computer-readable recording media.

Hereinafter, a certain exemplary embodiment is described in greater detail with reference to the accompanying Drawings. The exemplary embodiment described below shows a general or specific example. The numerical values, shapes, materials, elements, the arrangement and connection of the elements, steps, the processing order of the steps etc. shown in the following exemplary embodiment are mere examples, and therefore do not limit the scope of the appended Claims and their equivalents. Therefore, among the elements in the following exemplary embodiment, those not recited in any one of the independent claims are described as optional elements. Also, in the specification and the drawings, elements having substantially the same functional configuration are assigned the same reference marks and are not described to avoid redundancy.

Embodiment

[Configuration of Estimation Device 10A]

Figure 2:
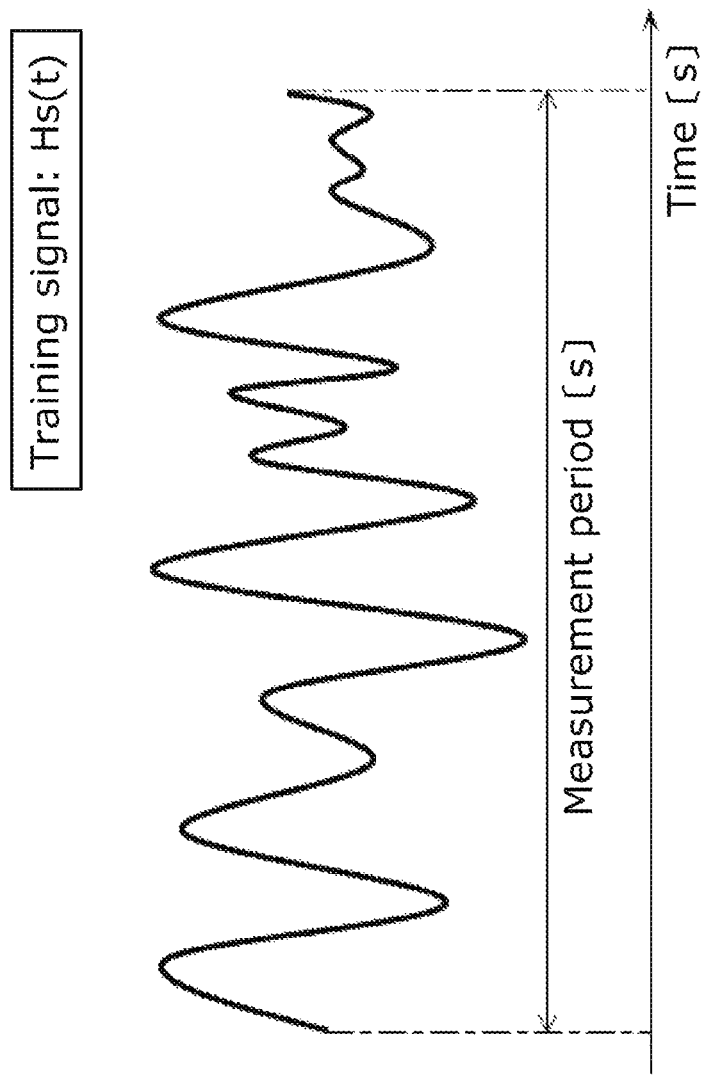
FIG. 2 is a diagram showing an example of the training signal shown in FIG. 1.
Figure 3:
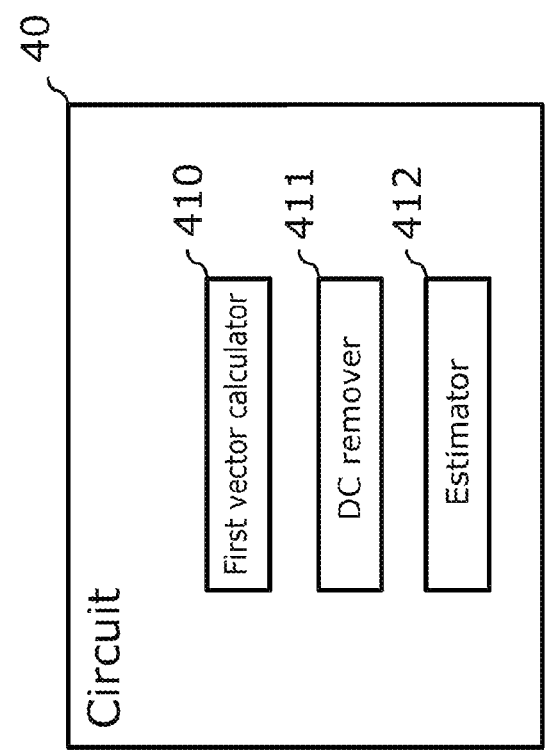
FIG. 3 is a configuration diagram showing an exemplary detailed configuration of the circuit shown in FIG. 1.

FIG. 1 is a configuration diagram showing an exemplary configuration of estimation device 10A according to the embodiment. FIG. 2 is a diagram showing an example of training signal 42 shown in FIG. 1. FIG. 3 is a configuration diagram showing an exemplary detailed configuration of circuit 40 shown in FIG. 1.

Estimation device 10A according to the present disclosure includes: M transmission antenna elements, where M is an integer greater than or equal to 1; N receivers each including a reception antenna element, where N is an integer greater than or equal to 3; circuit 40; and memory 41.

Each of the M transmission antenna elements transmits a transmission signal to predetermined range A1 that includes living body 50. The transmission signal is a high-frequency signal such as microwaves generated by a transmitter, etc.

Living body 50 is, for example, a person. Living body 50, which is a target to be estimated by estimation device 10A, is a living body to be authenticated or whose orientation is to be estimated.

Predetermined range A1 is a preliminarily defined range of a space that includes living body 50. Stated differently, predetermined range A1 is a space used by estimation device 10A to estimate living body 50.

Each of the M transmission antenna elements transmits, for example, a first transmission signal to predetermined range A1 that includes a first living body, which is living body 50 to be measured. Each of the M transmission antenna elements also transmits a second transmission signal to predetermined range A1 that includes a second living body, which is known living body 50 serving as training data.

The N receivers, each including a reception antenna element, are disposed to surround predetermined range A1. Using the reception antenna element, each of the N receivers receives, over a predetermined period, reception signals each including a reflection signal which is a transmission signal reflected by living body 50. For example, using the reception antenna element, each of the N receivers receives, over predetermined period T, first reception signals each including a reflection signal, which is a first transmission signal reflected by the first living body. Also, for example, using the reception antenna element, each of the N receivers receives training signals each being a second reception signal including a reflection signal, which is a second transmission signal reflected by the second living body, over a period that is K times longer than predetermined period T, where K is 2 or greater.

As shown in FIG. 1, estimation device 10A in the present embodiment includes, for example, eight transmitter-receivers 30A to 30H, circuit 40, and memory 41. Stated differently, the M transmission antenna elements and the N receivers may be configured as eight transmitter-receivers 30A to 30H. Note that the number of the transmitter-receivers is not limited to be eight.

[Transmitter-Receivers 30A to 30H]

In the present embodiment, eight transmitter-receivers 30A to 30H are disposed around predetermined range A1. Each of eight transmitter-receivers 30A to 30H transmits a transmission signal to predetermined range A1 that includes living body 50 such as a person, thereby receiving a reception signal that includes a reflection signal reflected by living body 50. Eight transmitter-receivers 30A to 30H may be disposed, for example, in a circular form at even intervals, or outside of predetermined range A1.

As shown in FIG. 1, transmitter-receivers 30A to 30H include corresponding antenna elements 31A to 31H. Using antenna elements 31A to 31H, transmitter-receivers 30A to 30H transmit transmission signals to predetermined range A1. More specifically, using antenna elements 31A to 31H, transmitter-receivers 30A to 30H emit microwaves as transmission signals to living body 50 such as a person. Note that transmitter-receivers 30A to 30H may transmit, using antenna elements 31A to 31H, unmodulated transmission signals or transmission signals that have undergone modulation processing.

To transmit modulated transmission signals, each of transmitter-receivers 30A to 30H may further include a circuit for performing modulation processing.

Using antenna elements 31A to 31H, transmitter-receivers 30A to 30H also receive, over a predetermined period, reception signals that include reflection signals, which are transmission signals reflected by living body 50. Transmitter-receivers 30A to 30H output the received reception signals to circuit 40. Note that each of transmitter-receivers 30A to 30H may include a circuit for processing the reception signals. In this case, each of transmitter-receivers 30A to 30H may transform the received reception signals into low-frequency signals by frequency transform. Note that each of transmitter-receivers 30A to 30H may demodulate the reception signals.

Subsequently, each of transmitter-receivers 30A to 30H outputs, to circuit 40, the signals obtained by frequency transform and/or demodulation processing.

In an example shown in FIG. 1, estimation device 10A includes eight transmitter-receivers 30A to 30H, which are transmitters and receivers having four antenna elements commonly used for transmission and reception, but the configuration of estimation device 10A is not limited to this. The number of transmitter-receivers 30A to 30H is not limited to eight, and thus may be, for example, N, where N is an integer greater than or equal to 3. Also, transmitters with M transmission antenna elements, where M is an integer greater than or equal to 1, and receivers with N reception antenna elements may be separately provided.

[Memory 41]

Memory 41 is an auxiliary storage device that includes a nonvolatile storage region. Examples of memory 41 include read only memory (ROM), a flash memory, a hard disk drive (HDD). Memory 41 stores, for example, information used for various processes of operating estimation device 10A.

As shown in FIG. 1, memory 41 stores training signals 42. Training signals 42 are signal waveforms preliminarily obtained for the second living body, which is known living body 50 that is (present) in predetermined range A1. More specifically, training signals 42 are (M×N) second reception signals, which is derived by multiplying M by N. Such (M×N) second reception signals are obtained by causing the N receivers to preliminarily receive second reception signals each including a reflection signal that is a second transmission signal transmitted from each of the M transmission antenna elements to the second living body and reflected by the second living body. Here, training signals 42 may be (M×N) second reception signals obtained by the N receivers preliminarily receiving second reception signals over a period that is K times longer than the predetermined period, where K is greater than or equal to 2.

In the present embodiment, the M transmission antenna elements and the N receivers include eight transmitter-receivers 30A to 30H as shown in FIG. 1. With reference to FIG. 2, an example of training signal 42 in such case will be described. Training signals 42 shown in FIG. 2 are exemplary reception signals received by a single receiver during a measurement period.

Training signals 42 shown in FIG. 2 are time response waveforms of a plurality of reception signals obtained by transmitter-receivers 30A to 30H preliminarily receiving reception signals that include reflection signals transmitted from antenna elements 31A to 31H to known living body 50 (second living body) present in predetermined range A1 and reflected from the surface of such second living body 50. Stated differently, training signals 42 shown in FIG. 2 represent the intensity of a plurality of reception signals obtained by transmitter-receivers 30A to 30H preliminarily receiving reception signals that include reflection signals during the measurement period. Here, the measurement period is a period that is K times longer than the foregoing predetermined period, where K is 2 or greater. Non-limiting examples of the measurement period is 120 seconds [s]. The measurement period is simply required to be longer than or equal to the heartbeat cycle of a person, and thus may be 3 seconds [s], 10 seconds [s], 30 seconds [s], etc.

Note that training signal 42 may be preliminarily obtained for each of a plurality of known second living bodies. In this case, each of a plurality of training signals 42 that correspond to a plurality of known second living bodies may be stored in memory 41 in association with estimation information used to estimate the corresponding second living body.

[Circuit 40]

Circuit 40, which is an estimator, performs various processes of operating estimation device 10A. Circuit 40 includes, for example, a processor that executes a control program and a volatile storage region (main storage device) used as a work area in executing the control program. The storage region is, for example, a random-access memory (RAM).

Circuit 40 temporarily stores the first reception signals obtained from the respective N receivers in the storage region for a predetermined period. Circuit 40 may temporarily store the phases and amplitudes of the first reception signals in such storage region for a predetermined period. In the present embodiment, circuit 40 temporarily stores the reception signals obtained from the respective transmitter-receivers 30A to 30H in the storage region for a predetermined period.

Note that circuit 40 may include a dedicated circuit for performing various processes of operating estimation device 10A. Stated differently, circuit 40 may be a circuit for performing software processing or may be a circuit for performing hardware processing. Circuit 40 may also include a nonvolatile storage region.

The following describes a functional configuration of circuit 40.

As shown in FIG. 3, circuit 40 includes first vector calculator 410, DC remover 411, and estimator 412. Note that DC remover 411 is not essential.

<First Vector Calculator 410>

More specifically, using the reception signals stored in the storage region of circuit 40 and the training signals stored in memory 41, first vector calculator 410 first calculates a propagation channel of each of the reception signals and each of the training signals:

[Math. 1]

$$H(t)$$

Here, each propagation channel

[Math. 2]

$$H(t)$$

to be obtained when a multiple-input and multiple-output (MIMO) array antenna that includes receiver $K_R$, transmitter $K_T$, $M_r$ reception antenna elements, and $M_t$ transmission antenna elements is disposed around living body 50 is represented as shown in Expression 1 and Expression 2:

[Math. 3]

$$H(t) = \begin{pmatrix} H^{(11)}(t) & \cdots & H^{(1K_T)}(t) \\ \vdots & \ddots & \vdots \\ H^{(K_R 1)}(t) & \cdots & H^{(K_R K_T)}(t) \end{pmatrix} \quad \text{(Expression 1)}$$

[Math. 4]

$$H^{(k_R k_T)}(t) = \begin{pmatrix} h_{11}^{(k_R k_T)}(t) & \cdots & h_{1M_t}^{(k_R k_T)}(t) \\ \vdots & \ddots & \vdots \\ h_{M_r 1}^{(k_R k_T)}(t) & \cdots & h_{M_r M_t}^{(k_R k_T)}(t) \end{pmatrix} \quad \text{(Expression 2)}$$

In Expression 1 and Expression 2, $K_R$ and $K_T$ represent a receiver number and a transmitter number, respectively, and $M_r$ and $M_t$ represent the antenna element number of each receiver and each transmitter, respectively.

[Math. 5]

$$h_{M_r M_t}^{(k_R k_T)}$$

represents a complex channel response from the $M_t$-th antenna of transmitter $K_T$ to the $M_r$-th antenna of receiver $K_R$, where t represents the observation time.

Subsequently, first vector calculator 410 calculates a frequency response matrix shown in Math. 7 of the propagation channels

[Math. 6]

$$H(t)$$

[Math. 7]

$$F(\omega)$$

The frequency response matrix

[Math. 8]

$$F(\omega)$$

is represented as in Expression 3.

[Math. 9]

$$F^{(k_R k_T)}(\omega) = \begin{pmatrix} f_{11}^{(k_R k_T)}(\omega) & \cdots & f_{1M_t}^{(k_R k_T)}(\omega) \\ \vdots & \ddots & \vdots \\ f_{M_r 1}^{(k_R k_T)}(\omega) & \cdots & f_{M_r M_t}^{(k_R k_T)}(\omega) \end{pmatrix} \quad \text{(Expression 3)}$$

Here, ω is a frequency range corresponding to the living body.

Subsequently, first vector calculator 410 converts the propagation channels

[Math. 10]

$$H(t)$$

and the frequency response matrix

[Math. 11]

$$F(\omega)$$

into vectors:

[Math. 12]

$$vec\{H(t)\}, vec\{F(\omega)\}$$

[Math. 13]

$$vec\{H(t)\}, vec\{F(\omega)\}$$

are represented as shown in Expression 4 and Expression 5, respectively, where T represents transpose.

[Math. 14]

$$vec\{H^{(k_R k_T)}(\omega)\} = \quad \text{(Expression 4)}$$

$$\left[h_{11}^{(k_R k_T)}(\omega) \ldots h_{M_r 1}^{(k_R k_T)}(\omega), \ldots, h_{1M_t}^{(k_R k_T)}(\omega) \ldots h_{M_r M_t}^{(k_R k_T)}(\omega)\right]^T$$

[Math. 15]

$$vec\{F^{(k_R k_T)}(\omega)\} = \quad \text{(Expression 5)}$$

$$\left[f_{11}^{(k_R k_T)}(\omega) \ldots f_{M_r 1}^{(k_R k_T)}(\omega), \ldots, f_{1M_t}^{(k_R k_T)}(\omega) \ldots f_{M_r M_t}^{(k_R k_T)}(\omega)\right]^T$$

Subsequently, first vector calculator 410 calculates a second matrix shown in Math. 17 from the vector matrix:

[Math. 16]

$$vec\{F(\omega)\}$$

[Math. 17]

$$R$$

The second matrix

[Math. 18]

$$R$$

is represented as shown in Expression 6, where $E[\{\ \}\{\ \}]$ is an ensemble average.

[Math. 19]

$$R^{(k_R k_T)} = E\left[vec\{F^{(k_R k_T)}(\omega)\} vec\{(F^{(k_R k_T)})^H(\omega)\}\right] \quad \text{(Expression 6)}$$

First vector calculator 410 then performs eigenvalue decomposition on the second matrix:

$$R \quad \text{[Math. 20]}$$

The eigenvalue decomposition is represented as shown in Expression 7, Expression 8, and Expression 9, where H represents complex conjugate transpose.

[Math. 21]

$$R^{(k_R k_T)} = U^{(k_R k_T)} \Lambda^{(k_R k_T)} \left(U^{(k_R k_T)}\right)^H \quad \text{(Expression 7)}$$

[Math. 22]

$$\Lambda^{(k_R k_T)} = \text{diag}\left[\lambda_1^{(k_R k_T)}, \ldots, \lambda_L^{(k_R k_T)}, \ldots, \lambda_{M_R M_T}^{(k_R k_T)}\right] \quad \text{(Expression 8)}$$

$$(\because \lambda_1 \geq \lambda_2 \geq \ldots, \lambda_L > \lambda_{L+1} = \ldots = \lambda_{M_R M_T})$$

[Math. 23]

$$U_1^{(k_R k_T)} = \left[u_1^{(k_R k_T)} \ldots, u_L^{(k_R k_T)}, \ldots, u_{M_r M_t}^{(k_R k_T)}\right] \quad \text{(Expression 9)}$$

Here,

[Math. 24]

$$\Lambda^{(k_R k_T)}$$

represents each diagonal element of the eigenvalues, and

[Math. 25]

$$U^{(k_R k_T)}$$

represents the eigenvector corresponding to an eigenvalue. Using each eigenvector

[Math. 26]

$$U^{(k_R k_T)}$$

and

[Math. 27]

$$vec\{H(t)\}$$

in Expression 4, first vector calculator 410 calculates first vectors:

[Math. 28]

$$y^{(k_R k_T)} = \begin{pmatrix} y_1^{(k_R k_T)} \\ \vdots \\ y_{M_r M_t}^{(k_R k_T)} \end{pmatrix} = \begin{pmatrix} \left(u_1^{(k_R k_T)}\right)^H vec\{H^{(k_R k_T)}(t)\} \\ \vdots \\ \left(u_{M_r M_t}^{(k_R k_T)}\right)^H vec\{H^{(k_R k_T)}(t)\} \end{pmatrix} \quad \text{(Expression 10)}$$

<DC Remover 411>

DC remover 411 calculates DC-removed first vectors by removing, from the first vectors of the reception signals and the training signals shown in Expression 10, the DC components that are noise components not required for the estimation of living body 50. DC remover 411 may store the calculated DC-removed first vectors in memory 41 or in the storage region of circuit 40.

DC remover 411 removes the direct current (DC) components from the first vectors by, for example, a method shown in Expression 11.

[Math. 29]

$$y_{DC}^{(k_R k_T)}(t) = y^{(k_R k_T)}(t) - \sum_{k=0}^{N-1} y^{(k_R k_T)}(k) / N \quad \text{(Expression 11)}$$

<Estimator 412>

Estimator 412 calculates correlation coefficients by removing the DC components from the first vectors calculated from the reception signals $$y_{T_L}^{(k_R k_T)}(t) \quad \text{[Math. 30]}$$

and the first vectors calculated from the training signals $$y_{D_L}^{(k_R k_T)}(t) \quad \text{[Math. 31]}$$

and then applying the following resultants to Expression 12:

$$y_{DC\_T_L}^{(k_R k_T)}(t), y_{DC\_D_L}^{(k_R k_T)}(t) \quad \text{[Math. 32]}$$

[Math. 33]

$$\rho(t, L) = \frac{\left| \sum_{k=0}^{N_T-1} \sum_{k_T=0}^{K_T} \sum_{k_R=1}^{K_R} y_{DC\_T_L}^{(k_R k_T)}(k) \left( y_{DC\_T_L}^{(k_R k_T)}(k + F_s t) \right)^* \right|}{\sqrt{\left| y_{DC\_T_L}^{(k_R k_T)}(k) \right|^2 \sum_{k=0}^{N_T-1} \sum_{k_T=0}^{K_T} \sum_{k_R=1}^{K_R} \left| y_{DC\_T_L}^{(k_R k_T)}(k + F_s t) \right|^2}} \quad \text{(Expression 12)}$$

Here, * represents complex conjugate.

Here, t represents the training data observation time, L represents a random eigenvalue number, NT represents the number of samples of test data reception signals, ND represents the number of samples of training signals, and FS represents the sampling frequency.

Here, Expression 13 and Expression 14 may be used to calculate correlation coefficients.

[Math. 34]

$$\rho(t, L) = \frac{\sum_{k_T=0}^{K_T} \sum_{k_R=1}^{K_R} \left| \sum_{k=0}^{N_T-1} y_{DC\_T_L}^{(k_R k_T)}(k) \left( y_{DC\_T_L}^{(k_R k_T)}(k + F_s t) \right)^* \right|}{\sqrt{\left| y_{DC\_T_L}^{(k_R k_T)}(k) \right|^2 \sum_{k=0}^{N_T-1} \sum_{k_T=0}^{K_T} \sum_{k_R=1}^{K_R} \left| y_{DC\_T_L}^{(k_R k_T)}(k + F_s t) \right|^2}} \quad \text{(Expression 13)}$$

[Math. 35]

$$\rho(t, L) = \frac{\left| \sum_{k_T=0}^{K_T} \sum_{k_R=0}^{K_R} \sum_{k=0}^{N_T-1} y_{DC\_T_L}^{(k_R k_T)}(k) \left( y_{DC\_T_L}^{(k_R k_T)}(k + F_s t) \right)^* \right|}{\sqrt{\left| y_{DC\_T_L}^{(k_R k_T)}(k) \right|^2 \sum_{k=0}^{N_T-1} \sum_{k_T=0}^{K_T} \sum_{k_R=1}^{K_R} \left| y_{DC\_T_L}^{(k_R k_T)}(k + F_s t) \right|^2}} \quad \text{(Expression 14)}$$

Subsequently, estimator 412 calculates the maximum value in time t direction for each eigenvalue L as shown in Expression 15.

[Math. 36]

$$\rho(L)_{max} = \max(\rho(t, L)) \quad \text{(Expression 15)}$$

Subsequently, estimator 412 adds the maximum values of the respective eigenvalues for the number of the used eigenvalues as shown in Expression 16. Estimator 412 performs the process shown in Expression 16 for each item of training data stored, and estimates the training data that gives the largest S as a correct living body.

[Math. 37]

$$S = \sum_{L=1}^{L'} \rho(L)_{max} \quad \text{(Expression 16)}$$

Here, instead of using Expression 16, a coefficient may be applied to each eigenvalue as shown in Expression 17:

[Math. 38]

$$S = \sum_{L=1}^{L'} \frac{1}{L^\alpha} \rho(L)_{max} \quad \text{(Expression 17)}$$

Here, training data that is obtained by changing the orientations of the living body enables the estimation of the orientation of the living body. Meanwhile, training data on different living bodies that is recorded with the orientations of the living bodies fixed enables the identification of the living body.

As described above, estimation device 10A shown in FIG. 1 is capable of estimating living body 50 by circuit 40 that processes the reception signals received by transmitter-receivers 30A to 30H.

[Operation of Estimation Device 10A]

Figure 4:
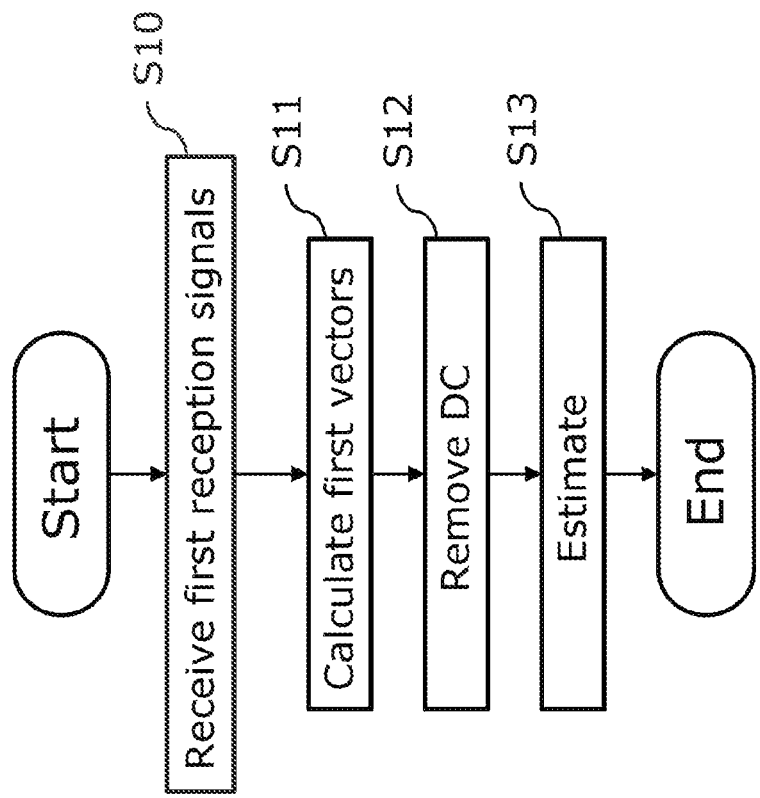
FIG. 4 is a flowchart of an exemplary operation performed by the estimation device according to the embodiment.
Figure 5:
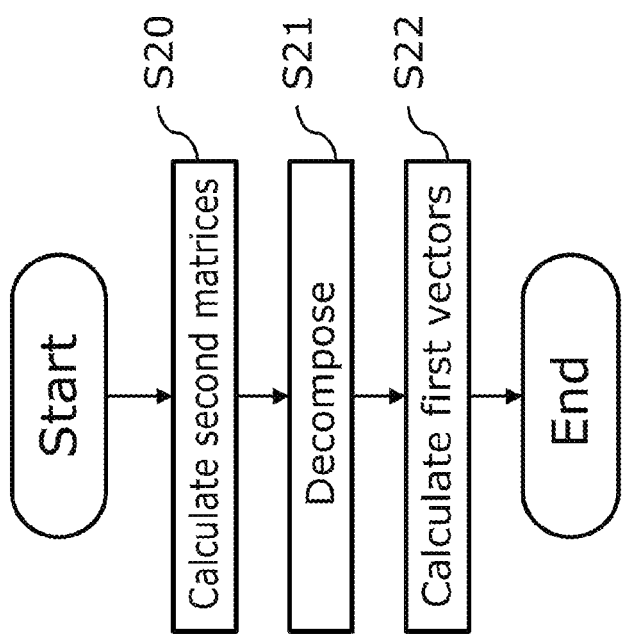
FIG. 5 is a flowchart of an exemplary detailed operation of step S11 according to the embodiment.
Figure 6:
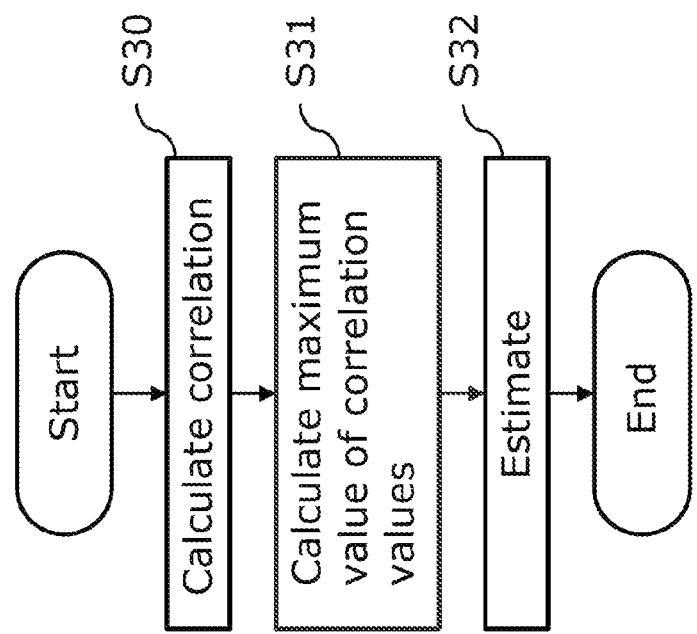
FIG. 6 is a flowchart of an exemplary detailed operation of step S13 according to the embodiment.

The following describes an operation performed by estimation device 10A with the above configuration. FIG. 4 is a flowchart of an exemplary operation performed by estimation device 10A according to the embodiment. FIG. 5 is a flowchart of an operation performed by first vector calculator 410 of estimation device 10A according to the embodiment. FIG. 6 is a flowchart of an operation performed by estimator 412 of estimation device 10A according to the embodiment.

First, estimation device 10A transmits M transmission signals and receives N reception signals (S10). More specifically, using the M transmission antenna elements, which is derived from (transmitter $K_T$)×(the number of transmission antenna elements $M_t$), estimation device 10A transmits first transmission signals to predetermined range A1 that includes the first living body. Subsequently, using the reception antenna element of each of the N receivers, which is derived from (receiver $K_R$)×(the number of reception antennas $M_r$), estimation device 10A receives, over a predetermined period, first reception signals each including a reflection signal that is the first transmission signal reflected by the first living body. In the present embodiment, transmitter-receivers 30A to 30H cause antenna elements 31A to 31H to transmit transmission signals to predetermined range A1 in a state that the first living body, which is living body 50 to be estimated, is located inside of predetermined range A1.

Using antenna elements 31A to 31H, transmitter-receivers 30A to 30H receive, over the predetermined period, first reception signals each including a reflection signal that is the first transmission signal reflected by the first living body.

Figure 7:
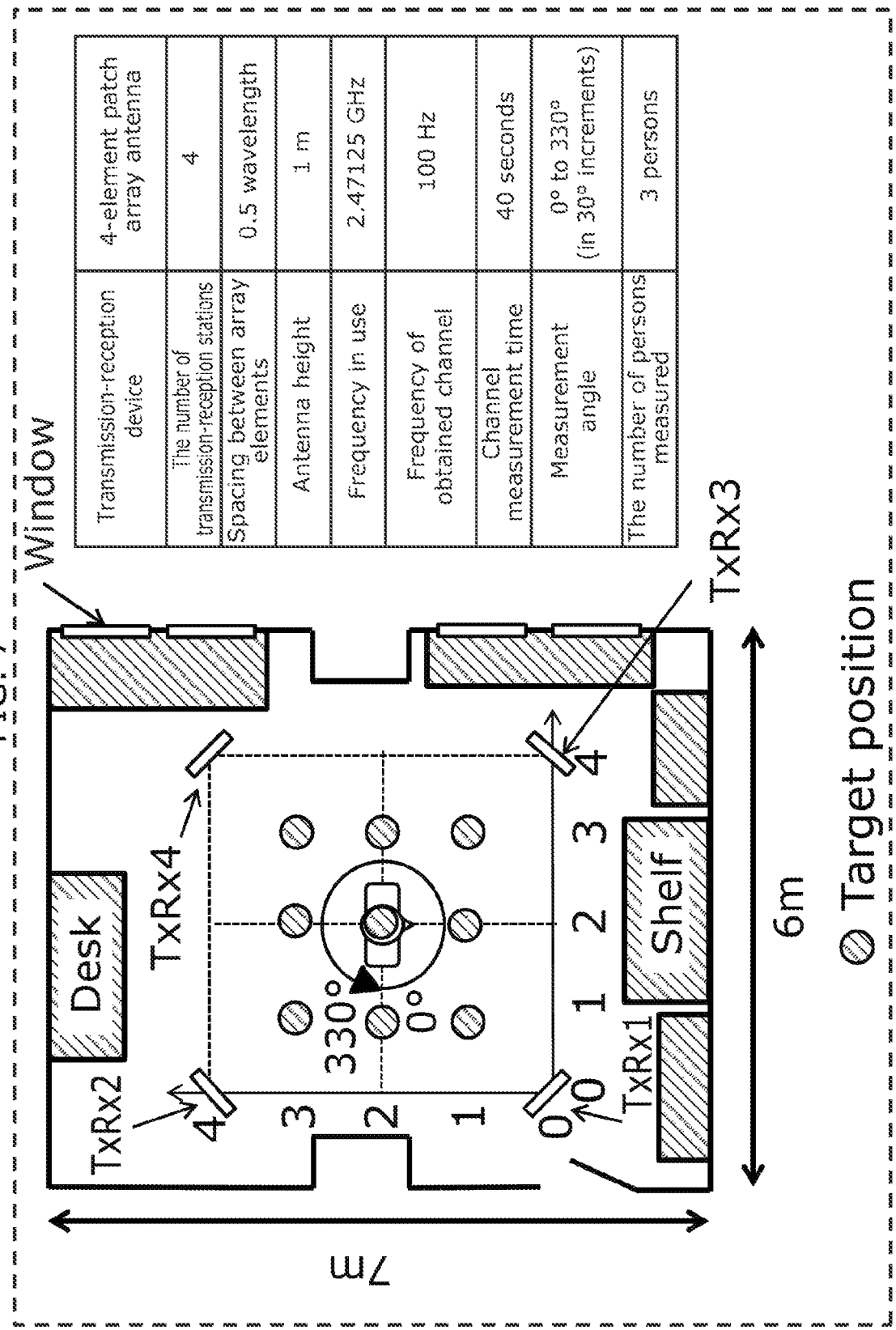
FIG. 7 is a diagram showing the environment used for a test that uses the estimation device according to the embodiment.
Figure 8:
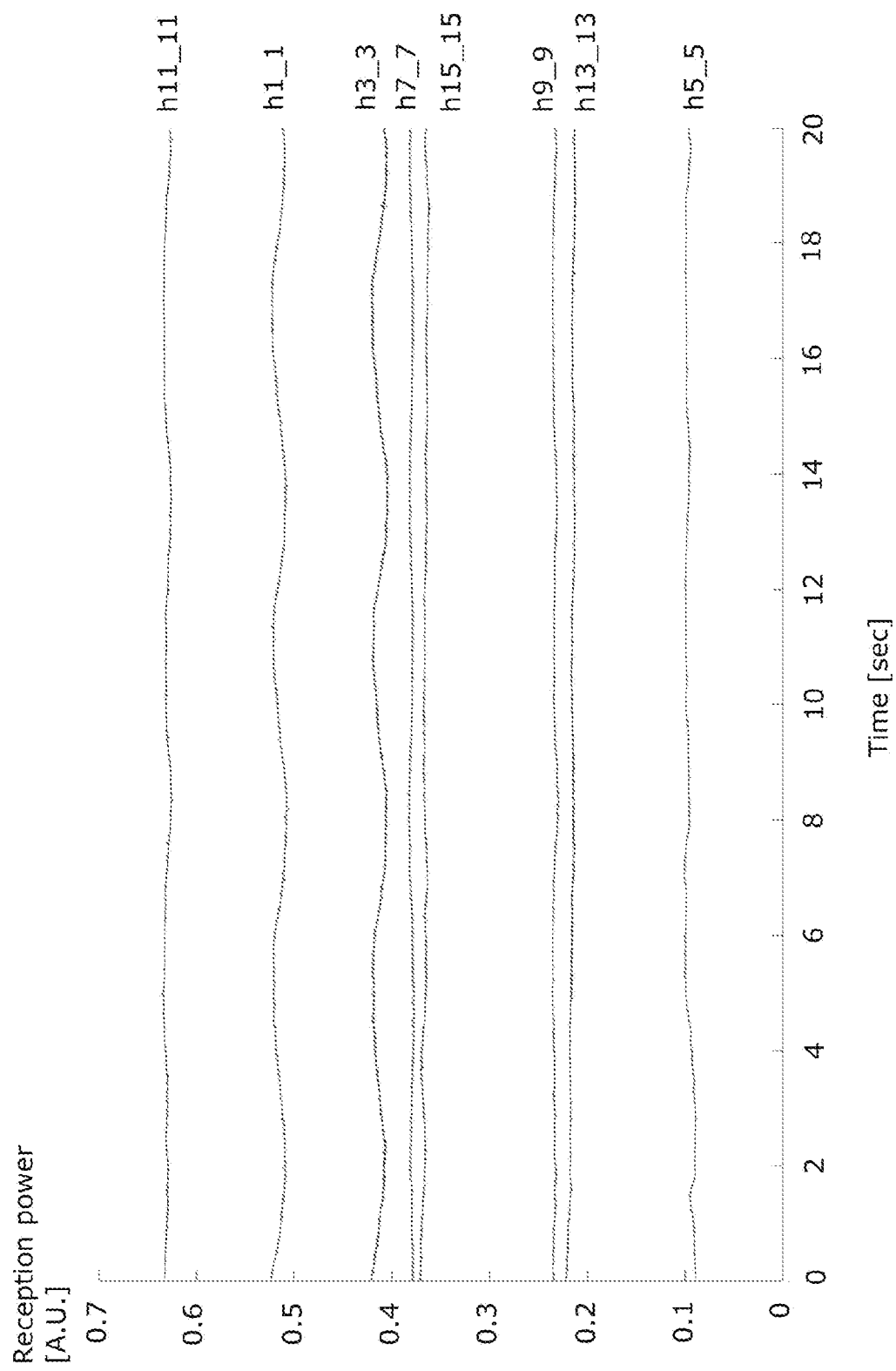
FIG. 8 is a diagram showing exemplary propagation channels calculated from reception signals received in the environment shown in FIG. 7.

Here, FIG. 7 is a diagram showing the environment in which an estimation test was conducted using estimation device 10A which is an example in the present embodiment. FIG. 8 is a diagram showing exemplary propagation channels calculated from the reception signals received in the environment shown in FIG. 7.

As shown in FIG. 7, in the estimation test in the present embodiment, estimation device 10A uses four transmitter-receivers that correspond to transmitter-receivers 30B, 30D, 30F, and 30H. Here, there may be eight receivers and transmitters as shown in FIG. 1, four receivers and transmitters, or any numbers greater than or equal to 2.

The four transmitter-receivers are disposed at the four vertices of a square with the side length of four meters (m), with test subject 50*a* located at the center. In the estimation test, test subject 50*a* corresponds to living body 50 to be estimated, i.e., the first living body. Also, four-element rectangular patch antennas are used as the reception antenna elements and the transmission antenna elements that correspond to antenna elements 31B to 31H.

More specifically, each of the eight reception antenna elements included in the four transmitter-receivers is a rectangular patch antenna located at the height of 0.9 m from the floor. Each of the eight transmission antenna elements included in the four transmitter-receivers is located one wavelength immediately above the microwaves of the corresponding reception antenna element. Here, the transmission antenna and the reception antenna may be a single antenna, or may be separately used.

Subsequently, estimation device 10A calculates first vectors from the first reception signals obtained in step S10 and training signals 42 stored in memory 41 (S11). A detailed process included in step S11 is shown in FIG. 5.

First, estimation device 10A reads, from memory 41, training signals 42, which are (M×N) second reception signals obtained by the N receivers preliminarily receiving reflection signals that are the second transmission signals transmitted from the M transmission antenna elements to the second living body, which is known living body 50, and reflected by the second living body.

Subsequently, estimation device 10A calculates a second matrix each from the first reception signals obtained in step S10 and training signals 42 read from memory 41 (S20).

Then, estimation device 10A performs eigenvalue decomposition on the second matrices (S21), and reorders the resulting eigenvalues in descending order of diagonal elements to calculate first vectors (S22). In the present embodiment, circuit 40 calculates the first vectors for both the first reception signals and training signals 42. Note that the present description uses eigenvalue decomposition in step S21, but singular value decomposition may be performed on the second matrices to calculate first vectors on the basis of the resulting singular values. In this case, the first vectors may be calculated as singular vectors by reordering singular values in descending order, or as eigenvectors.

Returning to FIG. 4, estimation device 10A then removes DC components from the first vectors of both the first reception signals and training signals 42 obtained in step S11 (S12).

Subsequently, estimation device 10A estimates the living body, using the first vectors of both the first reception signals and training signals 42 from which DC components have been removed in step S12 (S13). A detailed process included in step S13 is shown in FIG. 6.

Figure 9:
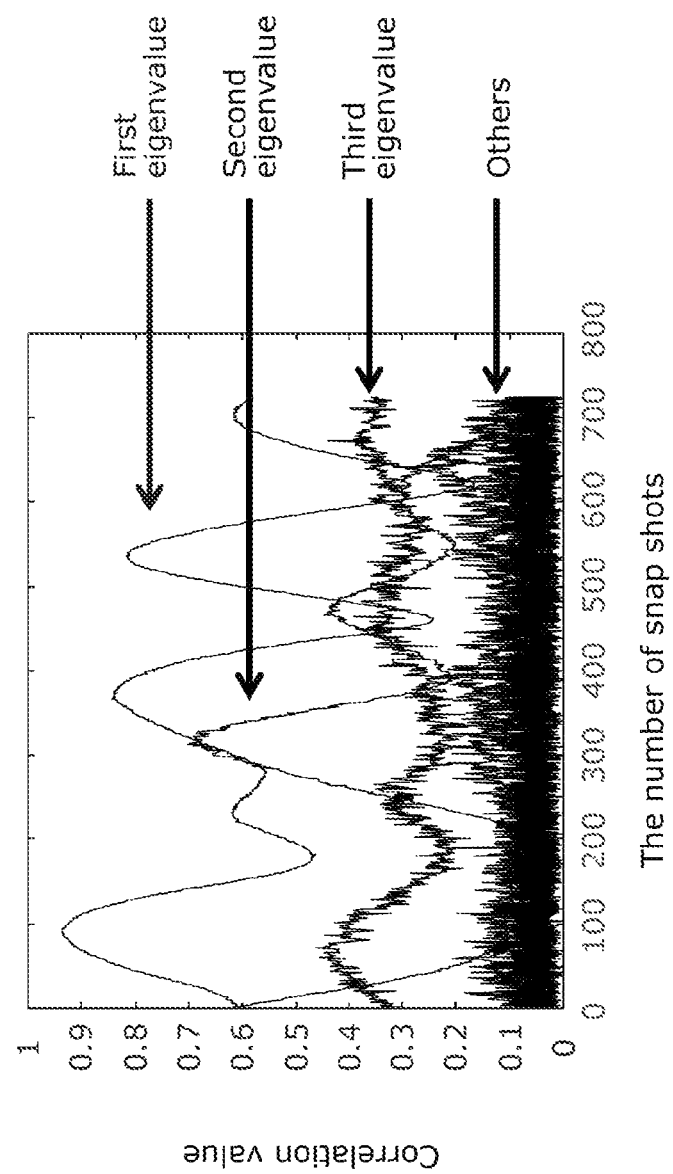
FIG. 9 is a diagram showing an exemplary result of correlation calculation performed after calculating first vectors of the propagation channels shown in FIG. 8.

Estimation device 10A calculates a correlation coefficient for each eigenvalue, using the first vectors of both the first reception signals and training signals 42 (S30). FIG. 9 shows correlation coefficients calculated for the respective eigenvalues. The first vectors are reordered in descending order of eigenvalues, such as a first eigenvalue and a second eigenvalue. As such, it is known from FIG. 9 that the degree of correlation is higher with a larger eigenvalue and lower with a smaller eigenvalue.

Subsequently, estimation device 10A determines the maximum value in temporal direction for each eigenvalue, and further calculates a total sum of the maximum values of the respective eigenvalues for the number of the used eigenvalues determined by a predetermined method (S31). Here, the number of the used eigenvalues may be, for example, on the order of two-thirds (⅔) of the total number of eigenvalues, such as eight and nine. Alternatively, eigenvalues may be selected which are greater than or equal to the average of correlation coefficients of the respective eigenvalues, or eigenvalues may be selected whose difference between the maximum and minimum values of the correlation coefficients is greater than or equal to a certain value.

Further, to calculate a total sum of the maximum values of the used eigenvalues, a total sum of the maximum values may be simply calculated or may be calculated using eigenvalues that have been sloped on eigenvalue basis.

Here, to slope eigenvalues on eigenvalue basis, slope coefficient $\alpha$ may be 1.7 or may be another coefficient. FIG. 10 shows the result of estimating the orientations of three living bodies as test subjects in an estimation test conducted by estimation device 10A shown in FIG. 7. The result shows that an average correctness is 75% or higher regardless of the positions where the three test subjects stand.

Subsequently, estimation device 10A performs living body estimation (S32). For the estimation of the orientation of a living body, estimation device 10A measures a training signal for each orientation of the living body, and estimates that the orientation that corresponds to the largest maximum value among those of the used eigenvalues is the orientation of the living body. For living body identification, estimation device 10A measures training signals in the same orientation that are located in a plurality of positions, measures a first signal of the second living body in the same orientation as the orientation in which the training signals have been obtained, calculates the maximum values of the used eigenvalues, and estimates that the training signal that corresponds to the largest maximum value among those of the used eigenvalues is the living body identified. At this time, the training signal that corresponds to the largest maximum value among the maximum values of the used eigenvalues may be estimated as the living body to be identified or the training signal that corresponds to an eigenvalue greater than or equal to a threshold may be estimated as the living body to be identified.

[Effect, Etc.]

In the environment used for a recognition test as shown in FIG. 7, estimation device 10A as an example of the present disclosure transmits transmission waves from transmitters or the antenna elements of the receivers disposed, for example, at four positions around living body 50, and receives reception signals. Subsequently, estimation device 10A: calculates second matrices from the training signals stored in memory 41 and the reception signals from living body 50 to be authenticated, which is test subject 50*a*; performs eigenvalue decomposition; reorders the resulting eigenvalues in descending order; calculates a first vector for each of the eigenvalues; removes the DC components from the first vectors; and calculates a temporal correlation of the first vectors by sliding correlation calculation.

First vectors having larger eigenvalues include a larger number of living body components. As such, it is possible to raise the signal-to-noise ratio of the living body components by narrowing down eigenvalues to be used.

Here, when test subject 50a and known living body 50 included in a training signal match, i.e., when known living body 50 and test subject 50a are in the same orientation, or when known living body 50 and test subject 50a are the same person in the same orientation, the maximum value of the correlation coefficients of sliding correlation becomes large. Meanwhile, when test subject 50a and known living body 50 included in a training signal are different, i.e., when known living body 50 and test subject 50a are in different orientations, or when known living body 50 and test subject 50a are different persons in the same orientation, the maximum value of the correlation coefficients of sliding correlation becomes small.

With this, it is possible for estimation device 10A to determine whether test subject 50a is in the same orientation as the orientation of known living body 50 included in a training signal, or whether test subject 50a and known living body 50 are the same living body, on the basis of the maximum value of the correlation coefficients calculated by sliding correlation calculation.

The reception signals obtained by the antenna elements of estimation device 10A are DC-biased. The DC bias is vulnerable to an individual difference of estimation device 10A and a delicate positional difference of living body 50, thus affecting an estimation rate. In view of this, estimation device 10A according to the present embodiment uses reception signals from which DC components have been removed to calculate a plurality of correlation coefficients. This improves the estimation rate.

As described above, estimation device 10A according to the present embodiment is capable of calculating a first vector on an eigenvalue basis from the training signals and the first reception signals that are measurement signals obtained from the reception antenna elements disposed around the first living body, and calculating a plurality of correlation coefficients by use of a selected number of values to be used. With this, it is possible to estimate the orientation of the living body and identifying an individual even under a condition that the living body and the antennas are relatively distant from each other and the signal-to-noise ratio of the living components is poor.

Further, it is possible to authenticate the living body by estimating whether the first living body and the second living body included in training data are in the same orientation or whether the first living body and the second living body are the same person in the same orientation, depending on whether the maximum value of a plurality of correlation coefficients exceeds a threshold.

Also, estimation device 10A according to the present embodiment removes the DC components from the first vectors by a predetermined method to calculate correlation coefficients. With this, it is possible to reduce from the reception signals the DC components, which are noise components not required for living body estimation, thus enabling the estimation of the living body to be effectively performed in a short time.

Further, estimation device 10A according to the present embodiment is capable of estimating living body 50, such as a person, by use of wireless signals such as microwaves. Stated differently, estimation device 10A according to the present embodiment is capable of estimating living body 50 such as a person, without needing to analyze images captured by a camera, etc. This thus enables the estimation of a person, while protecting the privacy of such person.

Each of the elements in the foregoing embodiment may be configured in the form of an exclusive hardware product, or may be realized by executing a software program suitable for the element. Each of the elements may be realized by means of a program executing unit, such as a CPU and a processor, reading and executing the software program recorded on a recording medium such as a hard disk or a semiconductor memory. Here, the software program for realizing the estimation device and so forth according to the foregoing embodiment are a program described below.

Stated differently, such program is a program that causes a computer to execute an estimation method performed by an estimation device that identifies a living body or estimates an orientation of the living body, wherein the estimation device includes: M transmission antenna elements each transmitting a first transmission signal to a predetermined range that includes a first living body, where M is an integer greater than or equal to 1; N receivers disposed to surround the predetermined range, where N is an integer greater than or equal to 3, the N receivers each including a reception antenna element that receives, over a predetermined period, a first reception signal that is the first transmission signal reflected by the first living body; and a memory that stores training signals which are (M×N) second reception signals obtained by causing each of the N receivers to preliminarily receive a second reception signal that is a second transmission signal transmitted from each of the M transmission antenna elements and reflected by a second living body; wherein the estimation method includes: calculating a first vector for each of the training signals and (M×N) first reception signals by respective predetermined methods, the (M×N) first reception signals being obtained by the N receivers each receiving the first reception signal; and calculating a plurality of correlation coefficients from the first vectors and identifying the first living body or estimating an orientation of the first living body by a predetermined method, using the plurality of correlation coefficients calculated.

The estimation device and others according to one or more aspects of the present disclosure have been described above on the basis of the embodiment, but the present disclosure is not limited to the embodiment. The present disclosure also includes a variation achieved by making various modifications to the embodiment that can be conceived by those skilled in the art without departing from the essence of the present disclosure and an embodiment achieved by combining elements included in different embodiments.

INDUSTRIAL APPLICABILITY

The present disclosure is applicable for use as an estimation device and an estimation method for estimating a living body by use of wireless signals. In particular, the present disclosure is applicable for use as: an estimation device included in a home appliance that performs control in accordance with a living body, a surveillance device that detects the intrusion of a living body, and so forth; and an estimation method.

REFERENCE SIGNS LIST

10A estimation device
30A-30H transmitter-receiver
31A-31H antenna element
40 circuit
41 memory
42 training signal
50 living body
50a test subject 410 first vector calculator
411 DC remover
412 estimator

The invention claimed is:

1. An estimation device that identifies a living body or estimates an orientation of the living body, by using electromagnetic wave, the estimation device comprising: M transmission antenna elements each transmitting a first electromagnetic transmission signal to a predetermined range that includes a first living body, where M is an integer greater than or equal to 1;
N receivers disposed to surround the predetermined range, where N is an integer greater than or equal to 3, the N receivers each including a reception antenna element that receives, over a predetermined period, a first reception signal that is the first electromagnetic transmission signal reflected by the first living body;
a memory that stores training signals which are M×N second reception signals obtained by causing each of the N receivers to preliminarily receive a second reception signal that is a second electromagnetic transmission signal transmitted from each of the M transmission antenna elements and reflected by a second living body;
a first vector calculator that calculates a first vector for each of the training signals and each of M×N first reception signals by respective predetermined methods, the M×N first reception signals being obtained by the N receivers each receiving the first reception signal; and
an estimator that selects a total number of values to be used which is determined from the first vector by a predetermined method, calculates a plurality of correlation coefficients, and identifies the first living body or estimates an orientation of the first living body by a predetermined method, using the plurality of correlation coefficients calculated.

2. The estimation device according to claim 1,
wherein the first vector calculator includes:
a second matrix calculator that calculates a second matrix from the first reception signals;
a decomposer that decomposes the second matrix by a predetermined method and reorders elements of the second matrix by a predetermined method, and
calculates the first vectors, using the elements of the second matrix that have been reordered and the training signals or the first reception signals.

3. The estimation device according to claim 2,
wherein the decomposer decomposes the second matrix into eigenvalues and reorders, in descending order, the eigenvalues that are diagonal elements.

4. The estimation device according to claim 2,
wherein the decomposer decomposes the second matrix into singular values and reorders, in descending order, the singular values that are diagonal elements.

5. The estimation device according to claim 1,
wherein the first vector calculator removes, by a predetermined method, a DC component from the first vectors calculated.

6. The estimation device according to claim 1,
wherein the estimator calculates, by a predetermined method, a total number of correlation functions to be used among a plurality of correlation matrices and calculates a total sum of correlation matrices for an amount equivalent to the total number of correlation functions to be used.

7. The estimation device according to claim 6,
wherein to estimate an orientation of the first living body, the estimator stores training signals for respective orientations of a living body, and estimates, as the orientation of the first living body, an orientation of one of the training signals that corresponds to a maximum of the total sum of the plurality of correlation matrices.

8. The estimation device according to claim 6,
wherein to identify the first living body, the estimator stores training signals in a same orientation for each living body, and estimates, as a living body identical to the first living body, one of the training signals that corresponds to a maximum of the total sum of the plurality of correlation matrices.

9. An estimation method performed by an estimation device that identifies a living body located far from the estimation device or estimates an orientation of the living body, by using electromagnetic wave,
wherein the estimation device includes:
M transmission antenna elements each transmitting a first electromagnetic transmission signal to a predetermined range that includes a first living body, where M is an integer greater than or equal to 1;
N receivers disposed to surround the predetermined range, where N is an integer greater than or equal to 3, the N receivers each including a reception antenna element that receives, over a predetermined period, a first reception signal that is the first electromagnetic transmission signal reflected by the first living body; and
a memory that stores training signals which are M×N second reception signals obtained by causing each of the N receivers to preliminarily receive a second reception signal that is a second electromagnetic transmission signal transmitted from each of the M transmission antenna elements and reflected by a second living body;
wherein the estimation method comprises:
calculating a first vector for each of the training signals and M×N first reception signals by respective predetermined methods, the M×N first reception signals being obtained by the N receivers each receiving the first reception signal; and
selecting a total number of values to be used which is determined from the first vector by a predetermined method, calculating a plurality of correlation coefficients, and identifying the first living body or estimating an orientation of the first living body by a predetermined method, using the plurality of correlation coefficients calculated.

* * * * *